United States Patent [19]

Osypka

[11] Patent Number: 4,550,737
[45] Date of Patent: Nov. 5, 1985

[54] INTRAVENOUSLY IMPLANTABLE ELECTRODE LEAD FOR USE WITH CARDIAC PACEMAKERS

[76] Inventor: Peter Osypka, Hornrain 31, D-7889 Grenzach-Wyhlen, Fed. Rep. of Germany

[21] Appl. No.: 541,389

[22] Filed: Oct. 12, 1983

[51] Int. Cl.$^4$ .............................................. A61N 1/04
[52] U.S. Cl. ................................... 128/785; 128/786; 128/419 P
[58] Field of Search .............................. 128/784–786, 128/419 P, 642

[56] References Cited

U.S. PATENT DOCUMENTS

| 4,026,303 | 5/1977 | Babotai | 128/419 P |
| 4,301,815 | 11/1981 | Doring | 128/786 |
| 4,407,303 | 10/1983 | Akerstrom | 128/419 P |
| 4,467,817 | 8/1984 | Harris | 128/786 |

FOREIGN PATENT DOCUMENTS

| 2506694 | 9/1975 | Fed. Rep. of Germany | 128/785 |
| 2533766 | 2/1977 | Fed. Rep. of Germany | 128/419 P |
| 2539553 | 3/1977 | Fed. Rep. of Germany | 128/785 |
| 1598793 | 9/1981 | United Kingdom | 128/419 P |

Primary Examiner—Lee S. Cohen
Attorney, Agent, or Firm—Peter K. Kontler

[57] ABSTRACT

An intravenously implantable electrode lead has a conductor whose rear end portion is connected to the casing of a cardiac pacemaker and whose front end has a stimulation surface. A sleeve-like screw surrounds the conductor immediately behind the stimulation surface and has a soft thread made of silicone rubber or polyurethane. The thread can yield during advancement of the screw through the openings of the trabecular network in the heart, and thereupon expand to reliably hold the stimulation surface in contact with a selected portion of the heart. The thread is continuous or discontinuous and tapers radially outwardly, and its height increases gradually from that end which is nearer to the stimulation surface toward the other end.

19 Claims, 4 Drawing Figures

INTRAVENOUSLY IMPLANTABLE ELECTRODE LEAD FOR USE WITH CARDIAC PACEMAKERS

CROSS-REFERENCE TO RELATED CASES

Commonly owned U.S. patent application Ser. No. 320,471 filed Nov. 12, 1981, and now abandoned, refers to a "Cardiac Pacemaker Electrode", and the commonly owned U.S. patent application Ser. No. 389,888 filed June 18, 1982, and now U.S. Pat. No. 4,466,690, refers to "A Connector for the Conductors of Implanted Medical Devices".

BACKGROUND OF THE INVENTION

The present invention relates to cardiac pacemaker systems in general, and more particularly to improvements in electrode leads which are used to transmit stimulation pulses from the casing of a cardiac pacemaker to a selected portion of the heart. Still more particularly, the invention relates to improvements in intravenous electrode leads.

It is already known to surround the conductor of an electrode lead with an insulating material which is inert to body media, and it is also known to provide such lead with a screw thread. The screw thread is disposed at the end which is distal from the casing of the pacemaker and its function is to maintain the head of the electrode lead in contact with the selected portion of the heart. Such electrode leads are disclosed, for example, in German Offenlegungsschrift No. 25 33 766 as well as in German Offenlegungsschrift No. 25 39 553. Each of these printed publications discloses a metallic screw which is threaded into and thus invariably insures the heart wall.

A modified electrode lead is disclosed in British Pat. No. 1,598,793 wherein the lead is provided with a conical anchoring element which is intended to be pushed into the trabecular network of the heart. German Offenlegungsschrift No. 25 06 694 discloses a further anchoring device which employs synthetic plastic bristles acting not unlike barbs which are pushed into and are thereupon supposed to expand in the trabecular network in order to maintain the head of the electrode lead in desired position. A drawback of the just mentioned proposals, which do not rely on screws or screw threads, is that the head of the electrode lead must be pushed through the vein and into the trabecular network of the heart. Another drawback of these proposals is that the diameter of the conical or bristle-like anchoring means appreciably exceeds the diameter of the insulating sheath of the lead and that such diameter increases in the direction of lengthwise movement of the lead during implantation into a human or animal body. The relatively large anchoring devices cannot pass through narrower openings or interstices of the trabecular network so that the head cannot be moved to a desired (optimum) position for transmission of stimuli to a selected portion of the heart.

OBJECTS AND SUMMARY OF THE INVENTION

An object of the invention is to provide a novel and improved electrode lead which has an anchoring device constituting or resembling a screw but avoiding the drawbacks and dangers of conventional anchoring devices which employ screw threads.

Another object of the invention is to provide an electrode lead for establishment of an intravenous connection between the casing of a cardiac pacemaker and the heart which is constructed and assembled in such a way that it can adequately anchor its head and the stimulation surface thereon in an optimum position in the selected portion of the heart without injuring the heart wall.

A further object of the invention is to provide an electrode lead of the above outlined character which can be reliably anchored in the trabecular network of the heart without resort to barbs, conical flanges and similar enlargements that prevent the penetration of the head of the lead into the trabecular network without damagihg the network during implantation.

An additional object of the invention is to provide a novel and improved method of implanting a portion of an intravenous electrode lead for use as part of a cardiac pacemaker system in the trabecular network of the heart.

Another object of the invention is to provide an electrode lead which is simple and relatively inexpensive, which can be used in conjunction with conventional pacemaker casings, which can be inserted into a vein in any one of heretofore known manners, and which can be used as a superior substitute for electrode leads that must be removed from a patient's body due to damage, malfunction or for other reasons.

An additional object of the invention is to provide an electrode lead which need not be forcibly advanced lengthwise in order to effect penetration of the stimulation surface on its head into contact with a selected portion of the heart.

Another object of the invention is to provide novel and improved anchoring means for use on or with an electrode lead of the above outlined character.

The invention resides in the provision of an intravenously implantable electrode lead for transmission of stimuli from a cardiac pacemaker to a selected portion of a patient's heart. The electrode lead comprises elongated flexible conductor means having a first end portion nearer to and a second end portion distal from the pacemaker and provided with a hemispherical or similarly configurated stimulation surface which can be brought into contact with the selected portion of the heart (the first end portion can be coupled to the casing of a pacemaker in a manner as disclosed, for example, in the aforementioned British Pat. No. 1,598,793), and means for anchoring the distal end portion of the conductor means in the heart (particularly in the trabecular network of the heart). In accordance with a feature of the invention the anchoring means comprises a screw which consists, at least in part, of a yieldable soft material capable of undergoing deformation during introduction into and travel through narrow openings or interstices of the trabecular network in response to rotation of the screw. Such screw surrounds the distal end portion of the conductor means behind the stimulation surface. The soft material can constitute a synthetic plastic substance and may contain or consist of silicone rubber or polyurethane. The electrode lead preferably further comprises an insulating sheath which surrounds the conductor means between the anchoring means and the first end portion of the conductor means, and the material of such insulating sheath is preferably inert to body media.

The screw can further include a sleeve which may be made of an insulating material and surrounds the respective part of the conductor means behind the stimulation surface; such sleeve is provided with one or more external screw threads, e.g., with a single screw thread which extends along an arc of at least 360°. The electrically insulating material of the sleeve which forms part of the anchoring means can be made of or can contain silicone rubber or polyurethane.

The screw thread or threads may be continuous or discontinuous. A discontinuous screw thread preferably comprises a helically arranged series of projections and has gaps which alternate with such projections. Each projection can have a substantially triangular cross-sectional outline, and each projection can have a pair of end faces which flank the adjacent gaps and are preferably disposed in planes extending at least substantially at right angles to the longitudinal directions of the respective portions of the screw thread.

The width of the gaps (as considered in the longitudinal direction of the screw thread) can equal or approximate the width of the projections.

The conductor means can be provided with a longitudinally extending passage and its distal end portion can be formed with a socket which is adjacent to and communicates with the respective end of the passage. Such passage can receive a so-called guide wire having a leading end portion which is received in the socket. The guide wire can serve to rotate the stimulation surface and the anchoring means to thereby advance the distal end portion of the conductor means through the openings of the trabecular network and to move the stimulation surface into contact with a selected portion of the heart. The socket can constitute a transverse slot in a shank forming part of a head which is formed with the stimulation surface, and the leading end portion of the guide wire then preferably resembles the working end of a screwdriver and is non-rotatably fitted into the slot.

The thread of the screw preferably tapers radially outwardly of the aforementioned sleeve so that its softness or yieldability increases in the same direction. Furthermore, at least one end portion of the thread (preferably the end portion which is nearer to the stimulation surface) increases in height from zero or practically zero to a maximum height at or close to the median portion of the thread. This facilitates introduction of the anchoring means through relatively narrow openings or interstices of the trabecular network during implantation of the electrode lead.

The novel features which are considered as characteristic of the invention are set forth in particular in the appended claims. The improved electrode lead itself, however, both as to its construction and the made of using the same, together with additional features and advantages thereof, will be best understood upon perusal of the following detailed description of certain specific embodiments with reference to the accompanying drawing.

DESCRIPTION OF THE PREFERRED EMBODIMENTS

Figure 1:
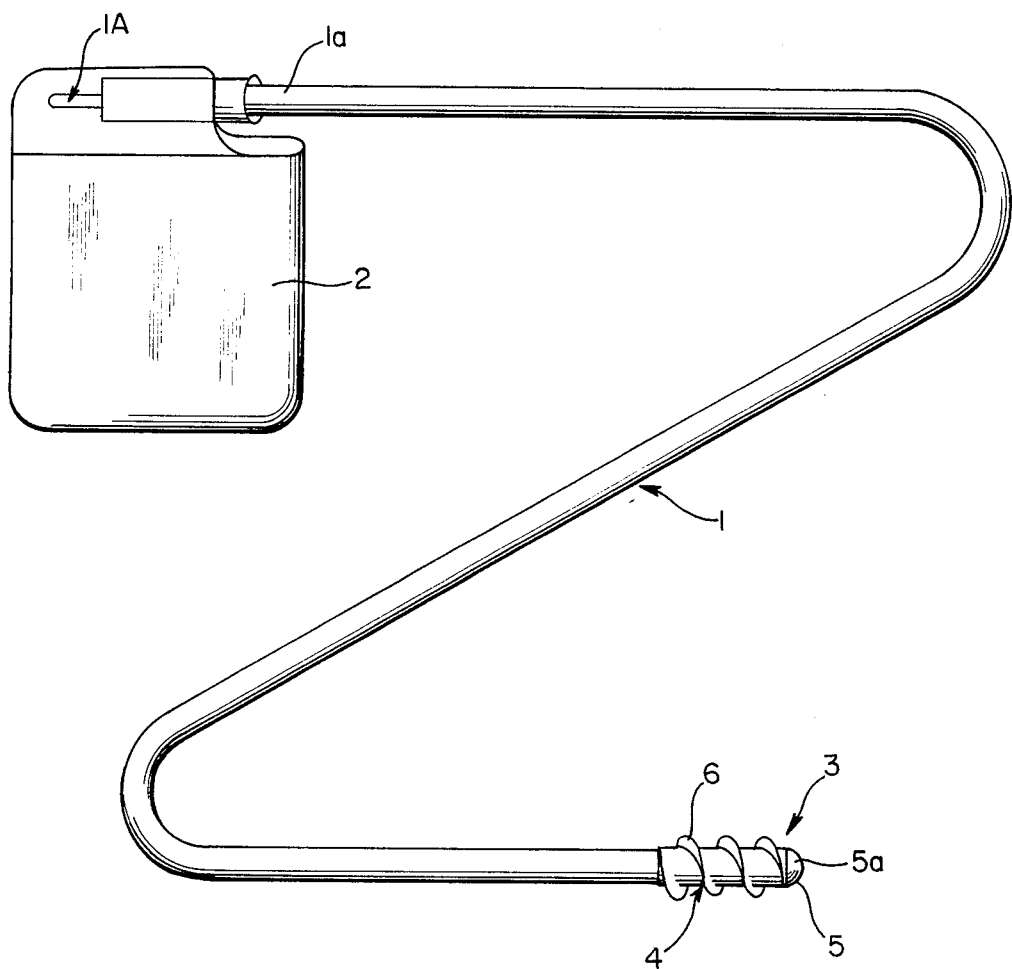
FIG. 1 is a schematic elevational view of a cardiac pacemaker casing and of an electrode lead which embodies one form of the invention.
Figure 2:
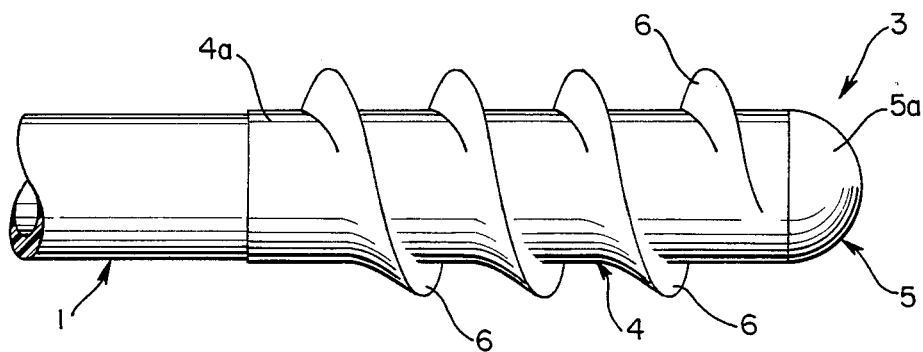
FIG. 2 is an enlarged view of the stimulation surface and of the distal end portion of the electrode lead, and further showing one form of anchoring means which is constructed and mounted in accordance with the present invention.
Figure 3:
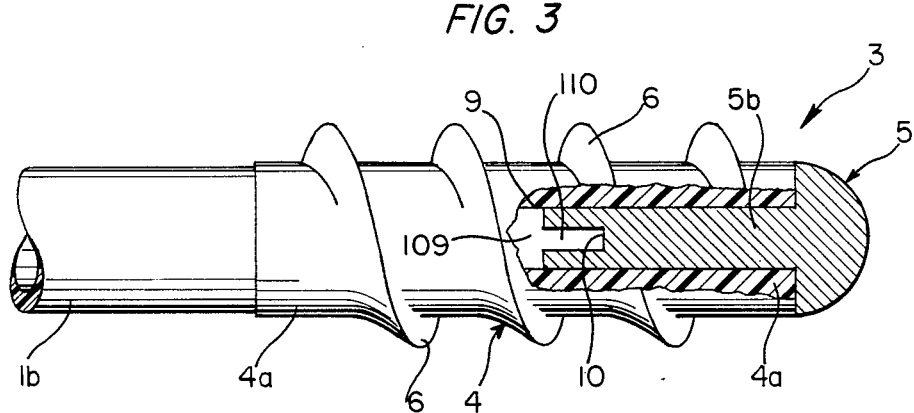
FIG. 3 illustrates the structure of FIG. 2 with a portion of the anchoring means and of the head which defines the stimulation surface broken away.

Referring first to FIGS. 1 to 3, there is shown a cardiac pacemaker system which comprises a casing 2 serving to accommodate an energy source and electronic pulse generating components, and a novel and improved electrode lead 1 including a flexible conductor 1A having a first end portion 1a coupled to the casing 2 and a second end portion 3 distal from the casing 2 and having a substantially hemispherical head 5 provided with an exposed stimulation surface 5a. The construction of the parts in the interior of the casing 2 forms no part of the invention.

In accordance with the invention, the electrode lead 1 further comprises a novel and improved anchoring means 4 which can be embedded in the trabecular network of the heart and is disposed immediately or shortly behind the stimulation surface 5a, as considered in the direction of propagation of stimulating pulses from the interior of the casing 2 toward the surface 5a. The anchoring means 4 comprises or constitutes a hollow screw which is made of a yieldable (preferably soft) material and includes a tabular sleeve or shell 4a. It has been found that silicone or polyurethane constitutes a highly satisfactory yieldably material which can be used for the making of the anchoring screw 4. The sleeve 4a constitutes an insulating means for the distal end portion 3 of the conductor 1A. The illustrated screw 4 has a single thread 6; however, it is equally within the purview of the invention to provide the screw 4 with a multiple thread. This screw is preferably formed with at least one complete thread 6, i.e., such thread preferably extends along an arc of at least 360 degrees.

FIG. 3 shows that the electrode lead 1 has an axial passage 9 which receives a so-called guide wire 109, and that the shank 5b of the head 5 has a rear end face provided with a socket 10 for reception of a complementary end portion 110 of the guide wire 109. The socket 10 is a transverse (diametrically extending) slot and, therefore, the end portion 110 of the guide wire 109 preferably constitutes a part which resembles the working end of a screwdriver and fits snugly into the socket 110. The guide wire 109 is rotated in a clockwise direction in order to drive the anchoring screw 4 home, i.e., to advance its thread 6 into the trabecular network in the selected portion of the heart so that the stimulation surface 5a is in an optimum position for transmission of pulses to the adjacent portion of the heart. Actually, the screw thread 6 penetrates into and is held in the openings of the trabecular network. This renders it unnecessary to exert an axial force upon the electrode lead 1 in order to move the stimulation surface 5a into contact with the selected portion of the heart; such axial advancement of the electrode lead (rather than an axial advancement which takes place as a result of rotation of the guide wire and concomitant rotation and forward movement of the screw 4) is not likely to establish a reliable contact between the selected portion of the heart and the stimulation surface. The guide wire 109 is caused to rotate in the passage 9 and to thereby rotate the screw 4 as well as the head 5. However, it is equally within the purview of the invention to omit the guide wire 109 and to drive the screw 4 home by rotating the entire electrode lead 1; in such pacemaker systems, the screw 4, the head 5 and the insulating sheath 1b of the lead 1 can rotate as a unit.

Figure 4:
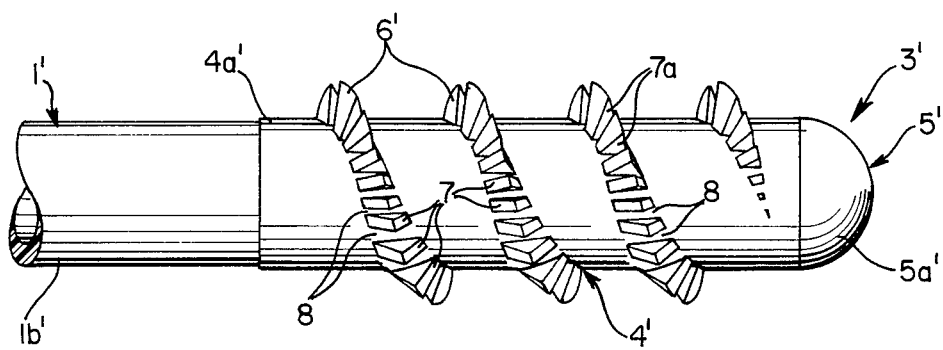
FIG. 4 is a view similar to that of FIG. 2 but showing a modified anchoring means.

FIG. 4 illustrates a portion of a modified electrode lead 1' with an insulating sheath 1b', a head 5' with a hemispherical stimulation surface 5a', and an anchoring screw 4' having an interrupted or discontinuous helical thread 6' including a series of spaced-apart projections 7 alternating with grooves or clearances 8. The width of the clearances or grooves 8 can approximate or match the width of the projections 7, as considered in the longitudinal direction of the thread 6', and each projection 7 can have a substantially triangular cross-sectional outline (as considered in a plane extending at right angles to the longitudinal direction of the respective portion of the thread 6'). Those surfaces (7a) of the projections 7 which flank the adjacent gaps 8 preferably extend at right angles to the longitudinal directions of the respective portions of the thread 6' and at right angles to the adjacent portion of the external surface of the tubular sleeve or shell 4a' of the screw 4'.

An advantage of the discontinuous thread 6' is that fibers of the trabecular network can penetrate into the gaps 8 when the screw 4' is fully introduced into the network so that the anchoring action is even more satisfactory than in the case of a screw (4) having a thread (6) with smooth flanks. It has been found that the subdivision of a thread into a series of helically arranged projections 7 does not interfere with convenient introduction of the stimulation surface 5a' into contact with the desired portion of the heart in response to rotation of the screw 4'. It is clear that the gaps 8 need not necessarily extend all the way to the cylindrical peripheral surface of the sleeve 4a' which forms part of the screw 4'. Relatively deep gaps 8 are desirable on the grounds that they allow for penetration of larger quantities of trabecular fibers and enhance the softness (yieldability) of the projections 7.

It is often sufficient if only the radially outer portion of the thread 6 or 6' exhibits a very pronounced yieldability. Such yieldability of the radially outermost portion of the screw thread 6 or 6' can be enhanced by proper configuration of the screw threads in a manner to be described below. Ready yieldability of the radially outermost portion of the screw thread is advantageous because it allows for advancement of the screw through relatively narrow openings of the trabecular network as well as because it enables the ridge in the region of the top land of the thread to even more accurately conform to the shape of the adjacent portion of the tissue when the electrode lead is fully implanted.

Irrespective of whether the improved anchoring screw has an uninterrupted thread 6 with smooth flanks or an interrupted thread 6', the thread preferably tapers outwardly, as considered in the radial direction of the respective sleeve 4a or 4a', i.e., the width of the top land of the thread 6 or 6' can be zero or a minute fraction of the width of the root of the respective thread. Such taper of the thread 6 or 6' enhances its deformability and reduces the likelihood of damage to the vein during implantation of the lead 1 or 1' and/or damage to the trabecular network in which the thread 6 or 6' is anchored in such position that the stimulation surface 5a or 5a' adequately contacts the selected portion of the heart. Moreover, the feature that at least the radially outermost part of the thread 6 or 6' is quite readily deformable facilitates introduction of the respective screw 6 or 6' into the trabecular network, i.e., the thread 6 or 6' is deformed in order to find its way through narrower openings or interstices of the trabecular network on its way to the final or fully inserted position. Moreover, once the readily deformable radially outermost portion of the thread 6 or 6' advances beyond a narrow portion or interstice of the trabecular network, it reassumes (or tends to reassume) its original shape with the result that the anchoring action of the screw 4 or 4' is even more satisfactory because the surface 5a or 5a' is even less likely to move out of contact with the selected portion of the heart as a result of movements of the heart and/or the flow of blood in the vein which accommodates the major portion of the lead 1 or 1'.

Another feature which is shared by the threads 6 and 6' is that each of these threads increases in height gradually from at least one of its two end portions, namely, from the end portion which is adjacent to the stimulation surface 5a or 5a' and preferably also from the end portion which is remote from such stimulation surface. In other words, the thread 6 or 6' reaches its full height (as considered radially of the sleeve 4a or 4a') in the median portion of the respective screw. Such configuration of the thread 6 or 6' also enhances the ability of the thread to conform to the anatomy in the interior of the heart.

Moreover, such configuration of the thread 6 or 6' further enhances its ability to find its way into narrow openings of the trabecular network. As can be seen in FIG. 4, the height and width of the leader of the screw thread 6' are zero or practically zero in the region immediately behind the stimulation surface 5a'. The height of the other end portion of the screw thread 6' may but need not increase from the locus at a maximum distance from the surface 5a' toward such surface (i.e., toward the median portion of the thread 6'). An advantage of a screw thread having a rear end portion whose height increases gradually toward the median portion is that the electrode lead 1' embodying such a screw can be more readily removed from the heart and from the vein if and when the need for removal of the lead arises.

An important advantage of the improved electrode lead 1 or 1' is that the distal end portion 3 or 3' of its conductor can be readily and reliably anchored in a selected portion of the heart, that such anchoring involves penetration of a screw thread 6 or 6' into a selected portion of the heart, but that the introduction of the screw thread does not exhibit the drawbacks and does not bring about the dangers of heretofore known (rigid) screw threads which are likely to perforate the heart wall with attendant extremely undesirable or fatal consequences. Another important advantage of the improved electrode lead is that the head 5 or 5' can be guided through wide or narrow as well as extremely narrow openings or interstices of the trabecular network without damaging the network because the thread 6 or 6' is capable of yielding in a number of different ways and of thereupon reassuming its normal shape in which it reliably holds the stimulation surface 5a or 5a' in requisite position for any desired period of time. Thus, the improved anchoring means 4 or 4' need not be provided with barbs or analogous projections which are used on heretofore known leads to prevent dislodging of the stimulation surface from its intended (optimum) position. Still further, the end portion 3 or 3' of the electrode of the improved electrode lead 1 or 1' can be properly introduced into the trabecular network of the heart without subjecting such network to extensive or pronounced deformation during introduction; this is due to the fact that the thread 6 or 6' can yield in a number of ways and in a practically infinite number of directions so that it can readily pass through narrow interstices of such network to thereupon expand and hold the surface 5a or 5a' against movement away from the adjacent portion of the heart. Still further, the introduction of the lead 1 or 1' into a vein in such a way that the surface 5a or 5a' comes in requisite contact with a selected portion of the heart is simple, convenient and consumes little time because the electrode lead need not be subjected to axial stresses but is merely rotated whereby the thread 6 or 6' takes care of forward movement at a desired rate in spite of its softness.

A further important advantage of the improved electrode lead 1 or 1' is its versatility. Thus, the first end portion of the conductor of the lead 1 or 1' (see the end portion 1a of the conductor 1A) can be provided with a connector or coupling member which can be fitted into the casings 2 of existing cardiac pacemakers. Moreover, the hemispherical shape of the stimulation surface 5a or 5a', in conjunction with yieldability of the thread 6 or 6', ensures that the improved electrode lead can be readily inserted intravenously without the likelihood of injuring the vein and/or the trabecular network and/or of puncturing the heart wall. In addition, the screw 6 or 6' can be rotated by rotating the entire conductor means 1 or 1' or in the aforedescribed manner through the medium of a guide wire which is rotatable in the major portion of the conductor means. Still further, the improved electrode lead can be readily removed from a vein by the simple expedient of rotating the screw 4 or 4' in a direction to move the stimulation surface 5a or 5a' away from the selected portion of the heart. The softness of the thread 6 or 6' enables the latter to readily conform to the configuration of the adjacent portion of the trabecular network.

An advantage of silicone and polyurethane is that such materials are sufficiently soft for the purposes of the present invention and also that such material is inert to body media. This is the reason that such materials are often used as insulators of conductors in electrode leads for cardiac pacemakers and are preferred for the making of sheaths 1b or 1b' and sleeves 4a or 4a'.

It will be noted that the improved electrode lead exhibits all advantages of conventional leads whose anchoring means are provided with screw threads but that the improved electrode lead avoids the drawbacks of conventional electrode leads. Thus, the lead 1 or 1' is highly unlikely to injure the heart wall during implantation. In order to further facilitate implantation of the improved electrode lead, the diameter of the screw 4 or 4' can be reduced to such an extent that it does not exceed at all, or exceeds only negligibly, the diameter(s) of the adjacent portion(s) of the lead. For example, the diameter of the sleeve 4a or 4a' can be even less than the maximum diameter of the head 5 or 5' so that only certain portions of the thread 6 or 6' will extend beyond the outline of the remaining major portion of the lead. The sleeve 4a or 4a' can constitute an integral part of the adjacent portion of the insulating sheath 1b or 1b' if the implantation takes place by rotating the entire electrode lead, i.e., if the latter does not comprise a wire guide 109 or an analogous insert-facilitating tool.

It has been found that the improved electrode lead can pass through openings which do not permit passage of conventional anchoring means with barbs, bristles, cones or analogous projections, and also that the improved electrode lead ensures reliable and wobble-free anchoring of the head 5 or 5' in an optimum position in the heart. Still further, the anchoring action is sufficiently reliable so that it is not affected by movements of the heart and/or by the flow of blood in the vein through which the electrode lead extends and/or by the flow of blood in the heart proper.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. An intravenously implantable electrode lead for transmission of stimuli from a cardiac pacemaker to a selected portion of a patient's heart, comprising elongated flexible conductor means for conducting the stimuli from the pacemaker to the selected portion of the heart, said conductor means having a first end portion adapted to be located nearer to and a second end portion adapted to be located distal from the pacemaker, and said second end portion being provided with a stimulation surface; and means for anchoring the distal end portion of the conductor means in the heart, including a screw consisting at least in part of yieldable soft material and surrounding the distal end portion of the conductor means behind the stimulation surface, said screw comprising a screw thread having a root adjacent to and a tip remote from the distal end portion of the conductor means, and said screw thread tapering in a direction from said root to said tip so that the latter is narrower than said root.

2. The electrode lead of claim 1, wherein said soft material is a synthetic plastic substance.

3. The electrode lead of claim 1, further comprising an insulating sheath surrounding said conductor means between said anchoring means and said first end portion and consisting of a material which is inert to body media.

4. The electrode lead of claim 1, wherein aid soft material contains silicone.

5. The electrode lead of claim 1, wherein said soft material contains polyurethane.

6. The electrode lead of claim 1, wherein said screw includes a sleeve surrounding the respective part of said conductor means and having an external surface provided with said screw thread.

7. The electrode lead of claim 6, wherein said sleeve consists of an electrical insulating material.

8. The electrode lead of claim 7, wherein said insulating material contains silicone rubber.

9. The electrode lead of claim 7, wherein said insulating material contains polyurethane.

10. The electrode lead of claim 1, wherein said screw thread is discontinuous.

11. The electrode lead of claim 10, wherein said thread comprises a helically arranged series of projections and has gaps alternating with said projections.

12. The electrode lead of claim 11, wherein said projections have a substantially triangular cross-sectional outline.

13. The electrode lead of claim 11, wherein each of said projections has a pair of end faces flanking the neighboring gaps and each extending at least substantially at right angles to the longitudinal direction of the respective portion of the thread.

14. The electrode lead of claim 11, wherein the width of said gaps, as considered in the longitudinal direction of the thread, equals or approximates the width of said projections.

15. The electrode lead of claim 1, wherein said conductor means has a longitudinally extending passage and said distal end portion has a socket adjacent to one end of said passage; and further comprising a guide wire provided in said passage and having an end portion non-rotatably received in said socket, said stimulation surface being arranged to rotate with said anchoring means in response to rotation of said guide wire.

16. The electrode lead of claim 15, wherein said socket is a transverse slot and said end portion of the guide wire resembles the working end of a screwdriver and is non-rotatably fitted into said slot.

17. The electrode lead of claim 1, wherein said screw thread has a first end adjacent to and a second end remote from said stimulation surface, the height of said thread increasing gradually from at least one of said ends toward the median portion thereof.

18. The electrode lead of claim 1, wherein said screw thread extends along an arc of at least 360°.

19. The electrode lead of claim 1, wherein said stimulation surface is a substantially hemispherical surface.

* * * * *